United States Patent [19]
Sutherland

[11] Patent Number: 4,850,970
[45] Date of Patent: Jul. 25, 1989

[54] TWO PART MASTITIS CANNULA CAP

[75] Inventor: Stephen F. Sutherland, Evansville, Ind.

[73] Assignee: American Home Products, Corp., N.Y.

[21] Appl. No.: 212,026

[22] Filed: Jun. 23, 1988

Related U.S. Application Data

[63] Continuation of Ser. No. 30,322, Mar. 26, 1987.

[51] Int. Cl.[4] ........ A61M 5/00
[52] U.S. Cl. ........ 604/117; 604/192
[58] Field of Search ........ 604/54, 73, 117, 192, 604/263, 278

[56] References Cited

U.S. PATENT DOCUMENTS 600,449 3/1898 Richardson ........ 604/192
1,436,707 1/1922 Easchke .
2,091,438 8/1937 Epstein .
2,529,836 11/1950 Darlington .
2,631,586 3/1953 Reilly .
2,848,997 8/1958 Miskel et al. .
2,908,609 10/1959 Aterno et al. .
2,922,420 1/1960 Cheng .
3,073,307 1/1963 Stevens .
3,234,945 2/1966 Waldman et al. .
3,294,063 12/1966 Broderick .
3,368,557 2/1968 Hassing et al. .
3,380,450 4/1968 Adelberger ........ 604/192
3,415,248 12/1968 Scott .
3,434,473 3/1969 Smith .
3,491,757 1/1970 Arce .
3,575,160 4/1971 Vass .
3,756,235 9/1973 Burke et al. .
3,825,003 7/1974 Kruck .
3,865,236 2/1975 Rycroft .
3,874,383 4/1975 Glowacki .
3,877,464 4/1975 Vermes .
3,882,866 5/1975 Zackheim .
3,888,234 6/1975 Clark .
3,889,673 6/1975 Dovey et al. .
4,009,716 3/1977 Cohen .
4,022,191 5/1977 Jamshidi .
4,040,421 8/1977 Young .
4,057,060 11/1977 Roth .
4,281,658 8/1981 Child .
4,300,545 11/1981 Goodnow et al. .
4,303,069 12/1981 Cohen .
4,308,859 1/1982 Child .
4,346,714 8/1982 Child .
4,359,044 11/1982 Child .
4,430,080 2/1984 Pasquini et al. .
4,453,930 6/1984 Child .
4,581,024 4/1986 Swenson .
4,659,330 4/1987 Nelson et al. .
4,710,171 12/1987 Rosenberg ........ 604/117
4,737,150 4/1988 Baeumie et al. .

FOREIGN PATENT DOCUMENTS 78000 8/1954 Denmark ........ 604/117

OTHER PUBLICATIONS

"Dry Treatment Technique May Affect Infection Rate"-Dairy, May 10, 1986, vol. 42, No. 6.
"How You Infuse Cows Can Spread Mastitis", S. C. Nickerson and R. L. Boddie, Hoards Dairyman, Nov. 10, 1985.

*Primary Examiner*—Stephen C. Pellegrino
*Assistant Examiner*—Ralph Lewis
*Attorney, Agent, or Firm*—Darby & Darby

[57] ABSTRACT

A two part mastitis cannula cap includes an outer cap and an inner cap. The inner cap is not as long as the cannula so that a free end of the cannula protrudes beyond an end face of the inner cap. This cannula protrusion is covered by the outer cap which is securable about the free end of the inner cap. Controlled depth partial insertion of the cannula into the teat canal of a dairy cow can be accomplished by removal of only the outer cap. Alternatively, full depth cannula insertion is accomplishable upon removal of the two parts of the cap.

12 Claims, 1 Drawing Sheet

FIG 1
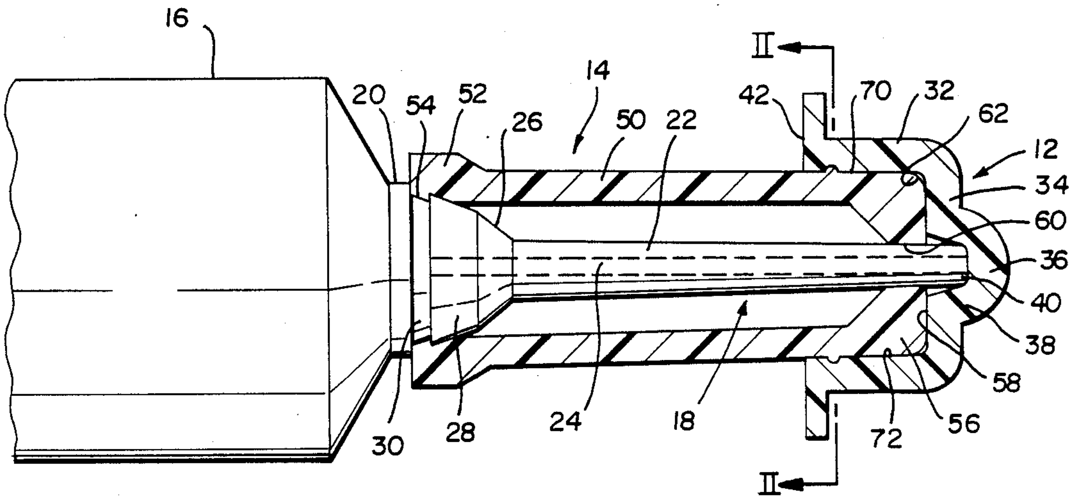
FIG 2
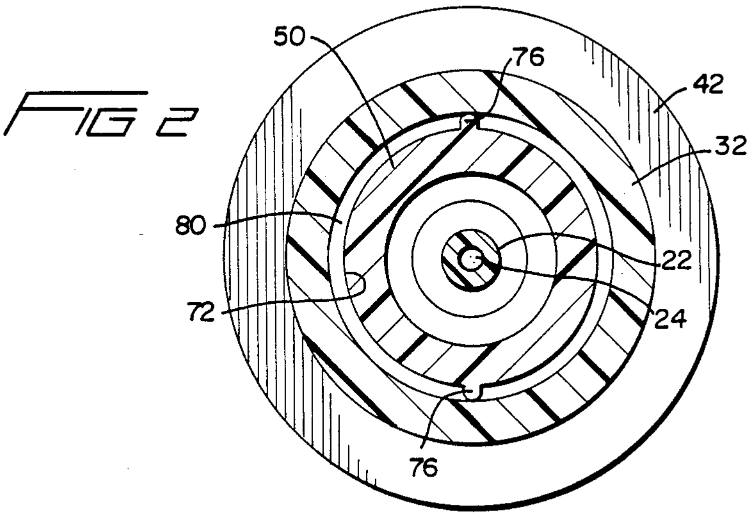
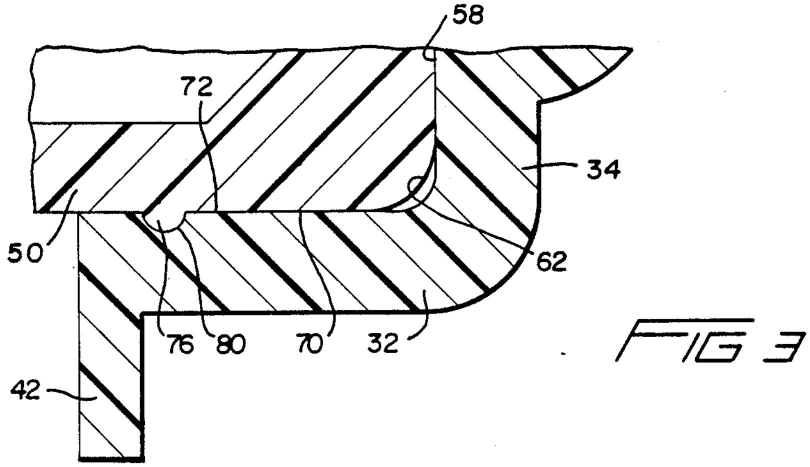
FIG 3

TWO PART MASTITIS CANNULA CAP

This is a continuation of application Ser. No. 030,322 filed Mar. 26, 1987.

FIELD OF THE INVENTION

The present invention is directed generally to a two part cap for a cannula. More particularly, the present invention is directed to a two part cap for the cannula of a mastitis infusion syringe. Most specifically, the present invention is directed to a two part, separable mastitis infusion cannula cap which is useable to limit the cannula's insertion depth into the teat canal of a dairy cow. The two part mastitis cannula cap includes an outer or overcap which is positionable at a free or distal end of an elongated inner cap. The outer cap is dimensioned to expose only a portion of the mastitis syringe cannula when this outer cap is removed from the inner cap. This insures that the cannula's insertion depth can be effectively limited to less than the length of the teat canal when only the outer cap is removed. Bacteria thus cannot be carried into the teat cistern by the mastitis treatment cannula equipped with the two part cap when only the outer cap is removed.

DESCRIPTION OF THE PRIOR ART

Bovine mastitis is a serious problem which afflicts large numbers of dairy cows. This mastitis, or inflammation of the cow's mammary gland, strikes substantial percentages of cows in dairy herds and has a detrimental effect on milk production and herd profitability. The generally followed method of treatment for bovine mastitis has been the administration of various antibiotic preparation into the cow's udder through the teat canal. A mastitis infusion syringe, which carries the antibiotic preparation, typically is equipped with an insertion cannula having a length of 20 to 25 mm. This cannula and syringe assembly is provided from the antibiotic supplier as a molded plastic, disposable unit which is prefilled with the treatment antibiotic. A single piece plastic cover, which typically snap fits onto the hub of the syringe at the base of the cannula, is used to cover the cannula prior to use. At the time of treatment, the protective cap is removed from the mastitis treatment syringe cannula and the cannula end is inserted into the cow's teat end, passed through the teat canal, and positioned within the teat cistern. Once the cannula has been so positioned, the syringe is utilized to deposit the treatment antibiotic directly into the cow's teat cistern.

Recent studies have suggested that the previously practiced full cannula insertion techniques may actually reduce rather than enhance the effectiveness of the treatment. This research has indicated that in some instances infection in the teat canal are carried into the teat cistern by the mastitis cannula during full cannula insertion. The cow's teat canal is approximately 1 cm in length and has a very narrow lumen. This canal helps to prevent bacteria from entering the cow's udder. Some bacteria may survive in secretions in the distal teat canal but are prevented from traveling the full length of the canal. These bacteria may be aided in their travel up the teat canal by the cannula as it passes through the canal during full cannula insertion. It has also been found that the teat canal or duct keratin layer, which helps control bacterial penetration into the udder, may be damaged by full cannula insertion. This full length cannula insertion may also cause the distal lumen to become larger than normal thus allowing increased bacterial travel and penetration. Bacteria which might otherwise exist for months in teat canal keratin without causing mastitis might enter the teat cistern area during full cannula insertion.

As a result of these above-discussed studies, there is now being utilized a partial insertion technique wherein the mastitis cannula is inserted into the teat end and up the teat canal only to a depth of generally about 3 mm. This technique appears to be beneficial in the treatment of mastitis but has made treatment procedures more time consuming for the dairyman. It is necessary that the cannula insertion depth be limited to generally about 3 mm to avoid the teat canal keratin damage and transport of bacteria from the teat canal along into the teat cister which was caused by the full insertion technique.

There presently exists no commercially prepared, readily useable yet disposable mastitis infusion syringe assembly which will allow the user to quickly and easily control the depth of cannula insertion thus rendering this partial insertion treatment effective. Individual measurements of each insertion depth are time consuming and are apt to be inaccurate. Mere guessing is even less accurate and may make the treatment of little value. It will thus be seen that a need exists for a mastitis treatment cannula assembly which will accurately, positively, and reproducably limit the depth of cannula insertion while not increasing treatment time, cost or the risk of contamination. The two part mastitis cannula cap assemby of the present invention provides a very satisfactory solution to the problem.

SUMMARY OF THE INVENTION

It is an object of the present invention to provide a mastitis treatment cannula and syringe assembly.

Another object of the present invention is to provide a mastitis cannula cover having a depth of insertion limiting capability.

A further object of the present invention is to provide a two part mastitis cannula cap.

Yet another object of the present invention is to provide a two part mastitis cannula cap having an insertion depth limiting outer cap.

Still a further object of the present invention is to provide a two part mastitis cannula cap which will allow full cannula insertion.

Yet still another object of the present invention is to provide a two part mastitis cannula cap usable with existing treatment syringes.

Even yet a further object of the present invention is to provide a two part mastitis cannula cap that is easy to handle, does not leak, is sterile, and will not harm the teat end.

As will be discussed in greater detail in the description of the preferred embodiment which is set forth subsequently, the two part mastitis cannula cap assembly in accordance with the present invention includes an inner cap which snaps onto the base of the cannula at a first end, and which has a relatively wide outer or distal end; and an outer cap which is removable carried on the distal end of the inner cap and which includes an outer rim or flange to facilitate removal. The outer cap covers generally about the outer 3 mm of the mastitis cannula which extends through an aperture at the distal end of the inner cap and, when removed, allows only partial depth insertion of the cannula into the teat canal. This depth of insertion is limited by the relatively large diameter of the distal end of the inner cap which also stabilizes the cannula against the teat end and prevents leakage during infusion of the treatment material during utilization of the partial insertion technique.

The two part mastitis cannula cap in accordance with the present invention includes an outer circumferential rim or flange which is formed as a part of the outer cap and which facilitates easy removal of this first cap. The herdsman or the like who is responsible for the treatment of the cattle can readily remove the outer cap, expose only that length of cannula required for partial insertion, and effect infusion of the treatment material in an efficient, predictable manner. Since the depth of cannula insertion is controlled by the abutment of the wide diameter distal end of the inner cap against the teat end, there is no chance for insertion of the cannula to an improper depth. Thus the partial insertion process is done to the same depth every time.

Should a full insertion procedure be desired, the complete cap assembly can be removed from the cannula by separation of the first or proximal end of the inner cap from the base of the cannula generally as has been accomplished in the past. Once the inner cap has been removed to expose the full length of the cannula, full insertion can be done in the conventional manner.

The two part mastitis cannula cap in accordance with the present invention provides the user with a choice. He can remove only the outer cap and utilize the cannula in a part insertion treatment procedure, or he can remove both the inner and outer caps to expose the full length of the mastitis control cannula for a full insertion procedure. The two part cap is usable with existing mastitis treatment cannula and syringe assemblies, is not expensive to manufacture and is thus disposable, and provides treatment flexibility not previously available. The two part mastitis cannula cap of the present invention is a significant advance in the art and is an effective tool in the control of bovine mastitis.

BRIEF DESCRIPTION OF THE DRAWINGS

While the novel features of the two part mastitis cannula cap in accordance with the present invention are set forth with particularity in the appended claims, a full and complete understanding of the invention may be had by referring to the detailed description of the preferred embodiment as is set forth hereinafter and as illustrated in the accompanying drawings in which:

FIG. 1 is a side elevation view, partly in section, of a mastitis treatment syringe and cannula utilizing the two part cap of the present invention;

FIG. 2 is a cross sectional view of the cannula and cap assembly taken along line II—II of FIG. 1; and FIG. 3 is an enlarged cross sectional side view of a portion of the outer and inner caps of the present invention.

DESCRIPTION OF THE PREFERRED EMBODIMENT

Turning initially to FIG. 1 there may be seen a two part mastitis cannula cap, generally at 10, in accordance with the present invention. Two part cap assembly 10 includes an outer or overcap 12 and an inner cap 14. This two part mastitis cannula cap 10 is shown in FIG. 1 in conjunction with a typical mastitis infusion syringe 16 that conventionally is a 10 ml disposable plastic syringe which is intended for a one time usage. A proximal or first end of an insertion cannula 18 is fused to a reduced diameter end 20 of syringe 16. Insertion cannula 18 typically is 20 to 25 mm in length and has a generally cylindrical hollow body 22 with a through bore 24. A generally conical shaped hub 26 is formed at first or distal end 28 of cannula 18 and this hub 26 is fused to the reduced diameter end 20 of syringe 16. An annular groove 30 is formed in the end 20 of syringe 16 adjacent cannula hub 26. This syringe 16 and cannula 18 assembly is a typical configuration in which a bovine mastitis treatment material is supplied. While the two piece mastitis cannula cap 10 in accordance with the present invention will be discussed for use with this syringe and cannula assembly, it will be understood that the size of the syringe, the overall length of the cannula and other similar structural characteristics of this syringe and cannula assembly, which form no part of the subject invention, could be changed.

Two part mastitis cannula cap 10 includes, as was indicated above, an outer cap 12 and an inner cap 14. As may be seen in FIG. 1, outer cap or overcap 12 is somewhat cup-shaped and has a generally cylindrical sidewall 32. A somewhat planar end wall 34 of outer cap 12 is joined to a first end of cylindrical sidewall 32 and has a central projection 36 which forms an interior concavity 38 that receives a free end or distal tip 40 of the insertion cannula 18. Concavity 38 has a depth of generally about 3 mm, depending on the length of free end 40 of cannula 22 which extends beyond inner cap 14, in a manner to be discussed shortly. Concavity 38 and cannula tip 40 are cooperatively sized to form a snug, leak resistant interfit. An enlarged annular outer flange 42 is joined to outer cap 12 at the second end of sidewall 32 opposite planar endwall 34. This outer flange 42 should be sufficiently large to facilitate grasping of outer cap 12 when this outer cap 12 is to be removed from inner cap 14. In the preferred embodiment, this annular outer flange 42 may have a diameter of generally about 10 to 20 mm.

Inner cap 14, as may be seen most clearly in FIG. 1, is generally in the shape of an elongated cylindrical sleeve having a tubular sidewwall 50. A snap end 52 of inner cap 14 has a radially inwardly extending lip 54 that is receivable in annular groove 30 formed at the junction of syringe end 20 and hub 26 of cannula 18. Detachment of the snap end 52 of inner cap 18 from syringe 16 is achieved by bending inner cap 14 to unseat lip 54 from groove 30.

Inner cap 14 terminates at its distal end 56 in an outer end face 58 that has a central aperture 60 through which the free end 40 of insertion cannula 18 passes. The outer end face 58 of inner cap 14 has a relatively wide diameter, generally in the range of about 5 to 7 mm and is smooth and somewhat rounded at its peripheral edges 62.

Outer cap 12 overlies the distal end 56 of inner cap 14, as may be seen in FIGS. 1 and 3. An inner surface 70 of outer cap sidewall 32 slidingly cooperates with an outer surface 72 of tubular sidewall 50 of inner cap 14 to effect retention of outer cap 12 on the distal end 56 of inner cap 14. Securement of inner cap 12 to outer cap 14 is enhanced by the cooperation of a pair of opposed protrusions 76, formed on the outer surface 72 of tubular inner cap sidewall 50, with a circumferential recess 80 cooperatively located in the inner surface 70 of outer cap sidewall 32. Alternatively, the number of protrusions 76 could be increased or a continuous rim (not shown) could be substituted. These protrusions 76, or rim, and circumferential recess 80 are sized so that a pulling or pushing force exerted on outer cap annular flange 42 will effect separation of outer cap 12 from inner cap 14 and not separation of inner cap 14 from syringe end 20. Separation of inner cap 14 from syringe end 20 is more easily accomplished by grasping the tubular sidewall 50 of inner cap 14 and by utilizing a bending force to unseat lip 54 from groove 30. Thus the two separating forces are of differing types so that separation will occur at the desired point.

In use, the two part mastitis cannula cap assembly in accordance with the present invention allows the dairy farmer, veterinarian, herdsman, or the like to practice whichever infusion procedure he feels will be more effective. Should partial insertion be desired, the outer cap's outer flange 42 is grasped and the outer cap 12 is removed. This exposes the free or distal end of insertion cannula. In accordance with present procedures, generally about 3 mm of the cannula free end 40 projects beyond the relatively wide diameter smooth end face 58 of inner cap 14. Since the teat canal of a cow is approximately 1 cm in length, the 3 mm projection of cannula free end 40 limits cannula insertion depth to a point within the teat canal and not into the teat cistern. Thus partial cannula insertion, to the correct depth can be quickly accomplished. The relatively large diameter outer end face 58 of the inner cap serves to stabilize the infusion cannula against the teat end while the free end 40 of the cannula is inserted partially into the teat canal. This wide end face also minimizes leakage of the material being infused. Since this end face 58 is smooth with gently rounded corners it will not harm the teat end. Additionally, since the teat canal is quite small in diameter, there is no possibility of the generally wide, large diameter end face 58 of the inner cap being inserted into the teat canal.

If full insertion of the mastitis treatment cannula is desired, this can readily be accomplished by removal of both the outer and inner caps as a single assembly. As discussed previously, this is accomplished by grasping the tubular sidewall 50 of the inner cap 14 and by exerting sufficient bending force to unseat the lip 54 on the snap end or proximal end 52 of the inner cap 14 from its cooperating groove 30 at the juncture of the syringe body 16 with the attached cannula 18. This exposes the entire length of cannula 18 so that full insertion of the cannula into the test cistern through the test canal can be accomplished.

The overall length of the two part mastitis cannula cap of the present invention will be generally in the range of 35 to 40 mm. This dimension is determined by the length of the cannula and is not particularly critical in itself. The length of the inner cap 14 with respect to the length of the cannula 18 is important because the difference in lengths between the shorter inner cap 14 and the longer cannula 18 determines the length of cannula free end tip 40 protrusion beyond the end face 58 of inner cap 14. As discussed above, a projection of generally about 3 mm is believed to be proper for optimal infusion of the mastitis treatment antibiotic preparation into the teat canal. The length of cannula tip 40 projection, in turn, dictates the depth of interior concavity 38 of projection 36 on the end wall 34 of the outer cap 12. The outer end of the distal tip 40 of cannula 18 should bear against the inner surface of this projection 36 to minimize any possible treatment material loss during shipment or handling and before the outer cap 12 is removed, either by itself during partial insertion, or with inner cap 14 during full insertion.

The two piece mastitis cannula cap in accordance with the present invention provides a safe, easy to use, accurately controllable and reproducable, inexpensive means to practice the partial cannula insertion technique which recent studies have suggested may be effective in the treatment of mastitis in dairy cows. At the same time, the two part cap structure affords the user an assembly which can be utilized for conventional full cannula insertion treatment, if desired. Thus the two part mastitis cannula cap of the present invention provides the freedom to select and use whichever of the two treatment procedures is deemed more desirable without sacificing ease of use, disposability, and package integrity.

While a preferred embodiment of a two part mastitis cannula cap in accordance with the present invention has been set forth fully and completely hereinabove, it will be obvious to one of skill in the art that a number of changes in, for example the size and shape of the syringe, the materials used for the syringe, cannula end cap, the overall length of the cannula and hence the overall length of the two part cap and the like may be made without departing from the true spirit and scope of the present invention which is accordingly to be limited only by the following claims.

What is claimed is:

1. A two part mastitis cannula cap for facilitating the controllable length insertion of a mastitis infusion syringe cannula into the teat canal portion of a teat of a dairy cow, said cap comprising:

an inner cap including a first snap end having means to attach said inner cap to the syringe, a generally elongated tubular side wall, a relatively large diameter, generally planar distal end face which is joined to a distal end of said inner cap tubular side wall, said generally wide distal end face being sized to prevent insertion of said inner cap into the teat canal while serving to stabilize said inner cap distal end face against the end of the teat during partial cannula insertion, said distal end face of said inner cap having a relatively small, central aperture, said central aperture being sized to allow a distal tip portion of the cannula to extend through said aperture, said inner cap having a length relative to the length of the mastitis infusion syringe cannula to allow said distal tip of the cannula to extend through said central aperture beyond said distal end face of said inner cap when said inner cap is attached to the syringe to thereby limit the length of said cannula which is exposed for insertion into the teat canal to a length less than the length of the teat canal; and an outer cap positionable about, and closely overlying said distal end of said inner cap, said outer cap having a generally planar end wall including a central projection which forms an interior concavity that receives said cannula distal tip, said interior concavity and said cannula distal tip being cooperatively sized to form a snug, leak resistant interfit, and further including a generally tubular sidewall, said outer cap sidewall being sized to overlie said inner cap tubular side wall to removably secure said outer cap to said distal end of said inner cap.

2. The two part mastitis cannula cap of claim 1 wherein said distal end face has a diameter of generally between 5 mm and 7 mm.

3. The two part mastitis cannula cap of claim 2 wherein the length of said inner cap relative to the length of the cannula allows the distal tip of the cannula to extend through said aperture by only about 3 mm.

4. The two part mastitis cannula cap of claim 3 wherein said distal end face of said inner cap is joined to said inner cap tubular side wall at a rounded peripheral edge.

5. The two part mastitis cannula cap of claim 1 wherein said snap end of said inner cap includes a radially inwardly directed lip, said lip being receivable in an annular groove in the syringe and forming said means to attach said inner cap to the syringe.

6. The two part mastitis cannula tip of claim 1 wherein said outer cap includes an outwardly extending flange.

7. The two part mastitis cannula cap of claim 6 wherein said flange is secured to said sidewall of said outer cap.

8. The two part mastitis cannula cap of claim 1 wherein said inner tubular sidewall includes at least two spaced protrusions and further wherein said outer cap sidewall has a recess on an inner face thereof, said recess and said protrusions cooperating to secure said outer cap to said inner cap.

9. In a mastitis infusion syringe having a blunt-tipped cannula sized in diameter and length to fit the teat canal portion of a teat of a dairy cow, a two part mastitis cannula cap for facilitating controllable length insertion of a mastitis infusion syringe cannula into the teat canal portion of a teat of a dairy cow, said cap comprising:

an inner cap including a first end having means to removably attach said inner cap to the syringe, a generally elongated tubular side wall and a second end having a distal end face with a diameter size to prevent insertion of said inner cap into a teat canal while serving to stabilize said distal end face against the end of a teat during cannula insertion, said distal end face having an aperture for permitting a distal tip portion of the cannula to extend through said aperture, said inner cap having a length smaller than that of the cannula, the length of the distal tip portion extending through said aperture, when the inner cap is attached to the syringe, being less than the length of a teat canal;

an outer cap for covering a cannula distal tip extending through said aperture of said inner cap, said outer cap being removably secured to said inner cap; and sealing means being provided in said cannula cap for preventing fluid leakage from said cannula cap;

whereby either the outer cap alone can be removed to expose the distal tip portion of the cannula or the outer and inner caps can be removed to expose the entire cannula.

10. A mastitis infusion syringe having a two part mastitis cannula cap as in claim 9 wherein said outer cap includes an internal recess and wherein said sealing means is provided by forming walls of said recess to closely interfit with the distal tip of said cannula to create a leak-resistant closure for said cannula distal tip.

11. A mastitis infusion syringe having a two part cannula cap as in claim 9 wherein said distal end face of said inner cap is relatively wide and planar in construction and wherein said central aperture in said distal end face is relatively small.

12. A method of selectively treating a dairy cow by partial or full insertion infusion of a bovine mastitis treatment medium, comprising the steps of:

providing a mastitis treatment syringe and cannula assembly containing a bovine mastitis treatment medium, said syringe and cannula assembly having a two part cannula cap including an inner cap and an outer cap secured to said inner cap, said inner cap having a length less than the length of a cannula and a distal end face through which the distal tip of the cannula projects;

selectively either (1) removing the outer cap and inserting the cannula tip into the end of a teat and into a teat canal of a dairy cow until the distal end face of the inner cap abuts the teat end, thereby placing the cannula distal tip within the teat canal; or (2) removing both the outer cap and inner cap from the cannula and inserting the cannula tip into the end of a teat and through the teat canal of a dairy cow, thereby placing the cannula distal tip within the teat cistern of the dairy cow; and activating the syringe to infuse the mastitis treatment medium into the teat canal or teat cistern of the dairy cow.

* * * * *

UNITED STATES PATENT AND TRADEMARK OFFICE
CERTIFICATE OF CORRECTION

PATENT NO. : 4,850,970

DATED : July 25, 1989

INVENTOR(S) : Stephen F. Sutherland

It is certified that error appears in the above-identified patent and that said Letters Patent is hereby corrected as shown below:

In column 2 line 16 change "cister" to --cistern--

In column 2 line 61, change "removable" to --removably--

In column 4 line 40, change "sidewwall" to --sidewall--

In column 5 line 46, change both occurrences of "test" to --teat--

In column 6 line 20, change "end" to --and--

In column 7 line 12 delete "tip" and insert --cap--

In column 7 line 33, change "size" to --sized--

Signed and Sealed this

Twenty-sixth Day of November, 1991

*Attest:*

HARRY F. MANBECK, JR.

*Attesting Officer* *Commissioner of Patents and Trademarks*